(12) United States Patent
Michaud et al.

(10) Patent No.: US 9,322,727 B2
(45) Date of Patent: Apr. 26, 2016

(54) TENSION METER FOR MEASURING A MECHANICAL TENSION ALONG A LONGITUDINAL DIRECTION IN A WELL AND RELATED SUBASSEMBLY AND METHOD

(71) Applicant: Geoservices Equipements, Paris Nord II (FR)

(72) Inventors: Christophe Michaud, Soignolles en Brie (FR); Vincent Chatelet, Paris Nord II (FR)

(73) Assignee: GEOSERVICES EQUIPEMENTS, Paris Nord II (FR)

( * ) Notice: Subject to any disclaimer, the term of this patent is extended or adjusted under 35 U.S.C. 154(b) by 14 days.

(21) Appl. No.: 14/390,388

(22) PCT Filed: Apr. 10, 2013

(86) PCT No.: PCT/EP2013/057508
§ 371 (c)(1),
(2) Date: Oct. 2, 2014

(87) PCT Pub. No.: WO2013/153126
PCT Pub. Date: Oct. 17, 2013

(65) Prior Publication Data
US 2015/0075291 A1 Mar. 19, 2015

(30) Foreign Application Priority Data
Apr. 10, 2012 (EP) .................................... 12163534

(51) Int. Cl.
*G01N 3/08* (2006.01)
*G01L 5/06* (2006.01)
(Continued)

(52) U.S. Cl.
CPC ... *G01L 5/06* (2013.01); *G01L 1/02* (2013.01); *G01L 5/04* (2013.01); *G01N 2203/0048* (2013.01); *G01N 2203/0232* (2013.01)

(58) Field of Classification Search
CPC .............. G01N 2203/0048; G01N 2203/0232; G01L 9/0002; G01L 5/06; G01L 1/02; G01L 5/04
USPC .......... 73/152.48, 152.59, 826, 837, 832, 828
See application file for complete search history.

(56) References Cited

U.S. PATENT DOCUMENTS 1,901,962 A  3/1933 Greene
3,722,584 A * 3/1973 Nelson .................. E21B 21/001
166/350

(Continued)

*Primary Examiner* — Max Noori

(57) ABSTRACT

Tension meter (82) for measuring a mechanical tension (F1) along a longitudinal direction (L) between a first element (84) and a second element (80) deployed in a well containing a fluid (50) having a fluid pressure, the tension meter comprising:—a bar (108) comprising a first portion (152), a second portion (154), and a measurement portion (156), and—a hollow member (110) defining a first chamber (169) surrounding the measurement portion, the bar being free to expand within the hollow member under the mechanical tension (F1) to be measured. The measurement portion includes at least one strain gauge (172). The tension meter includes first sealing elements for keeping the first chamber at a first chamber pressure, the measurement portion being subject to a compression force (F2) due to a difference between the fluid pressure and the first chamber pressure. The tension meter includes means for converting the fluid pressure into a traction force (F3) applied on the second portion (154), wherein the compression force (F2) and the traction force (F3) compensate. Related subassembly and method.

14 Claims, 5 Drawing Sheets

(51) Int. Cl.
  *G01L 1/02* (2006.01)
  *G01L 5/04* (2006.01)

(56) References Cited

U.S. PATENT DOCUMENTS

| | | | |
|---|---|---|---|
| 4,402,229 A | 9/1983 | Byrne | |
| 4,778,355 A * | 10/1988 | Holland | F04B 47/08 417/378 |
| 5,460,251 A * | 10/1995 | Jeffries | E05F 1/16 188/282.1 |
| 6,679,341 B2 * | 1/2004 | Bloom | E21B 4/18 175/104 |
| 7,652,592 B2 | 1/2010 | Le Briere et al. | |
| 7,980,787 B1 * | 7/2011 | Trent | E21B 19/002 166/355 |
| 8,109,157 B2 * | 2/2012 | Kanayama | E21B 49/10 73/863.72 |
| 9,175,554 B1 * | 11/2015 | Watson | E21B 43/128 |

* cited by examiner

TENSION METER FOR MEASURING A MECHANICAL TENSION ALONG A LONGITUDINAL DIRECTION IN A WELL AND RELATED SUBASSEMBLY AND METHOD

The present invention relates to a tension meter for measuring a mechanical tension along a longitudinal direction between a first element and a second element deployed in a well containing a fluid having a fluid pressure, the tension meter comprising:
- a first part intended to be attached to the first element,
- a second part intended to be attached to the second element,
- a bar extending longitudinally between the first part and the second part, the bar comprising a first portion mechanically connected with the first part, a second portion mechanically connected with the second part, and a measurement portion extending longitudinally between the first portion and the second portion, and
- a hollow member receiving at least the measurement portion, the hollow member and the measurement portion defining a first chamber surrounding the measurement portion, the second portion being outside the first chamber and the bar being free to expand within the hollow member under the mechanical tension to be measured, The present invention also relates to an associated subassembly and an associated method.

The well is for example a bore hole intended to collect/store a fluid in the ground, such as oil or natural gas, water or carbon dioxide.

To perform various complex operations in a well, such as for example opening and closing valves, placing elements such as packings, or perforating a wall, it is known to lower a subassembly in the well at an extremity of a line. In order to monitor these operations, in particular for avoiding the breaking of the line, it is also known to use a tension meter, for example extending between a tool of the subassembly and a line head, in order to measure the mechanical tension between the tool and the line head along a longitudinal direction of the well.

Indeed, the tension measured on the line at the surface may be very different from the tension applied between the tool and the line at the connection point between these elements. This difference can be significant in some operations, such as recovery of the subassembly in a deviated well.

Known tension meters include an elastic member intended to be submitted to the mechanical tension to be measured, and a Linear Variable Differential Transformer (LVDT) to transform a displacement of the elastic member into an electrical signal representative of the mechanical tension. The elastic member and the LVDT are hosted in a protective casing defining a chamber.

When introduced in a well, the tension meter is usually surrounded by a column of fluid under pressure comprising particles. As it may operate deep inside the well, for example at a depth of 2 to 3 km, the fluid hydrostatic pressure may be quite high, typically in a 0 to 1000 bar range. The fluid hydrostatic pressure applies on the measuring probe. Since the mechanical tensions to be measured possibly fall on the low side of this range, there is a need for neutralizing the potential impact of such a high pressure on the elastic member. In order to do so, the chamber includes an opening to let the outside fluid flow in the chamber. As a result, the elastic member is completely surrounded by the fluid. The mechanical impact of the fluid pressure on the elastic member is reduced, so that the mechanical tension can be efficiently measured.

Unfortunately, the fluid entering the chamber being muddy and loaded with particles, there is a risk that the elastic member and/or the LVDT becomes blocked or even damaged. To prevent this from happening, the tension meter must be opened and the chamber thoroughly cleaned after each use, when the subassembly is brought to the surface. This operation is tedious and time consuming.

One aim of the invention is therefore to provide a tension meter that is accurate and easier to use, while remaining economical.

To that end, the invention relates to tension meter of the aforementioned type, wherein:
- the measurement portion includes at least one strain gauge,
- the tension meter includes first sealing elements for keeping the first chamber at a first chamber pressure, the measurement portion being subject to a compression force due to a difference between the fluid pressure and the first chamber pressure, and
- the tension meter includes means for converting the fluid pressure into a traction force applied on the second portion, wherein the compression force and the traction force compensate.

The tension meter according to the invention may comprise one or more of the following feature(s), taken alone or according to all technically possible combination(s):
- the second portion of the bar comprises a chamber section, and an intermediate section extending between the chamber section and the measurement portion along the longitudinal direction and intended to be in hydrostatic contact with the fluid, and the hollow member and the chamber section define at least one second chamber, the tension meter having second sealing elements for keeping the second chamber at a second chamber pressure, approximately equal to the first chamber pressure;
- the hollow member includes at least one opening for allowing the hydrostatic contact of the intermediate section with the fluid;
- the hollow member and the intermediate section of the bar define an intermediate fluid chamber having at least an opening for enabling the fluid to enter the intermediate fluid chamber, the intermediate fluid chamber extending between the first chamber and the second chamber along the longitudinal direction, the first sealing elements separating the intermediate fluid chamber from the first chamber, the second sealing elements separating the intermediate fluid chamber from the second chamber;
- the means comprises at least one second chamber defined by the hollow member and a chamber section of the second portion of the bar, the tension meter having second sealing elements for keeping the second chamber at a second chamber pressure, approximately equal to the first chamber pressure; at least one opening for allowing a hydrostatic contact of an intermediate section the second portion of the bar with the fluid, the intermediate section extending between the chamber section and the measurement portion along the longitudinal direction; and an intermediate fluid chamber defined by the hollow member and the intermediate section of the bar, said opening enabling the fluid to enter the intermediate fluid chamber, the intermediate fluid chamber extending between the first chamber and the second chamber along the longitudinal direction, the first sealing elements separating the intermediate fluid chamber from the first chamber, the second sealing elements separating the intermediate fluid chamber from the second chamber;

the second portion include an outside section protruding outside of the hollow member, the second portion being mechanically connected with the second part by the outside section;

the first sealing elements include a first gasket, located between the measurement portion and the intermediate section, the first sealing elements defining a first opening of the first chamber, the first opening having a first surface in projection in a plane transverse to the longitudinal direction; the second sealing elements include a second gasket, located between the intermediate section and the chamber section, the second sealing elements defining a second opening of the second chamber, the second opening having a second surface in projection in a plane transverse to the longitudinal direction; and the second sealing elements include a third gasket, located between the chamber section and the outside section, the second sealing elements defining a third opening in the second chamber, the third opening having a third surface in projection in a plane transverse to the longitudinal direction, the second surface being larger than the third surface;

the difference between the second surface and the third surface defines a hydrostatic surface of the second chamber which is approximately equal to the first surface;

the second part is mechanically connected with the intermediate section of the bar, the hollow member being closed longitudinally towards the second part by a closing portion extending radially, the second chamber extending between the closing portion and the chamber portion of the bar along the longitudinal direction;

the first sealing elements include a first gasket, located between the measurement portion and the intermediate section, the first sealing elements defining a first opening of the first chamber, the first opening having a first surface in projection in a plane transverse to the longitudinal direction; and the second sealing elements include a second gasket located between the intermediate section and the chamber section, the second sealing elements defining a second opening in the second chamber, the second opening having a second surface in projection in a plane transverse to the longitudinal direction;

the second surface is approximately equal to the first surface;

the first chamber pressure is intended to be approximately equal to the atmospheric pressure.

The invention also relates to a subassembly intended to be deployed in a well with a line along a longitudinal direction, the subassembly comprising at least a first element including a tool, and a second element including a connecting head, characterized in that the subassembly comprises a tension meter as described above, the tension meter connecting the first element with the second element.

The invention also relates to a method for measuring a mechanical tension along a longitudinal direction between a first element and a second element, the method comprising the following steps:
  providing a tension meter as described above,
  attaching the first part to the first element,
  attaching the second part to the second element, and
  deploying the first element and the second element in a well containing a fluid having a fluid pressure,
characterized in that it also comprises the steps of:
  keeping the first chamber at a first chamber pressure,
  subjecting the measurement portion to said compression force due to a difference between the fluid pressure and the first chamber pressure, and
  converting the fluid pressure into said traction force applied on the second portion using said means of the tension meter, wherein the compression force and the traction force compensate.

The invention will be better understood upon reading the following description, provided solely as an example and done in reference to the appended drawings, in which:

FIG. 1 shows an intervention assembly 10.

Figure 1:
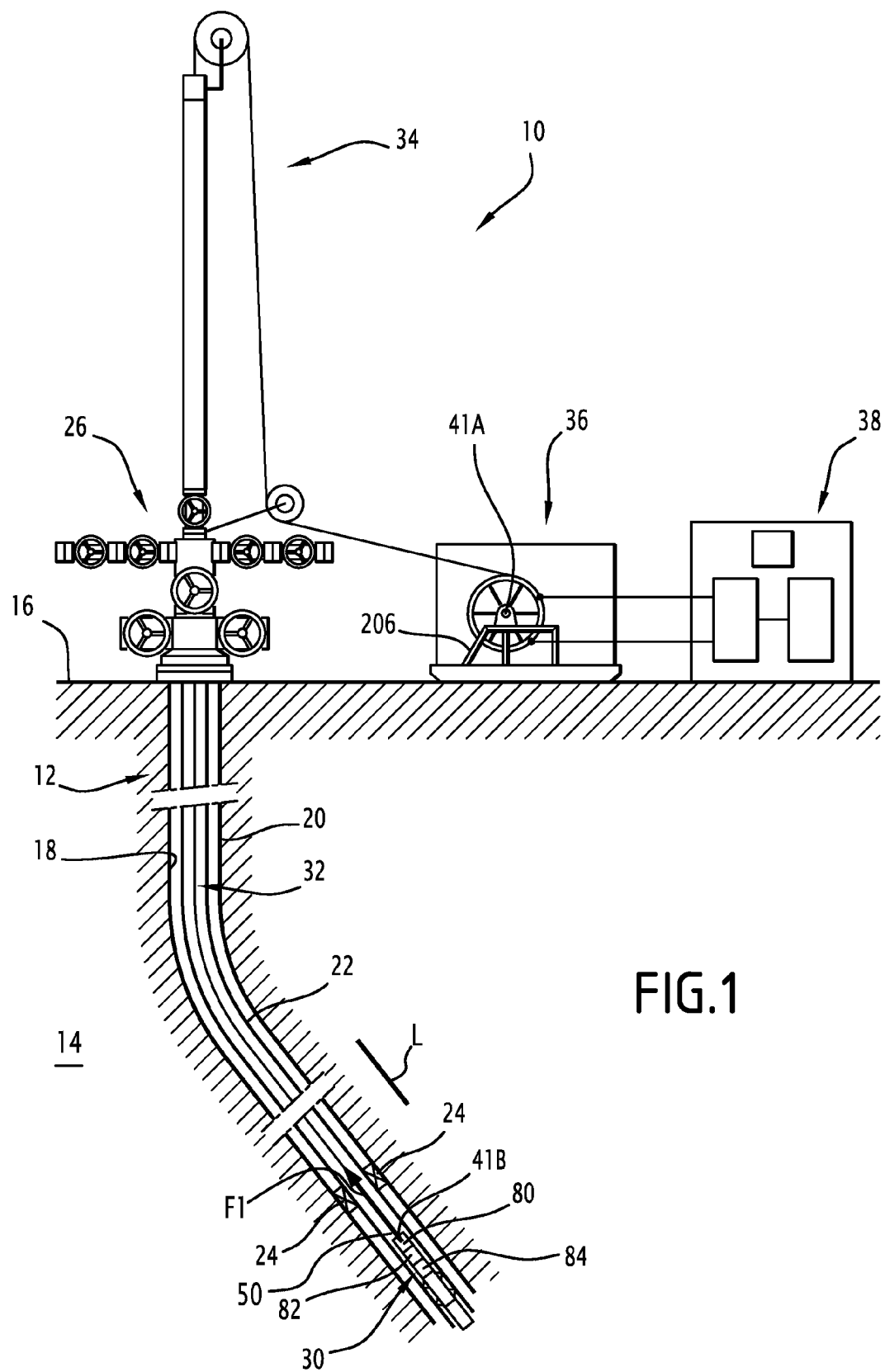
FIG. 1 is a schematic cross-sectional view of a well receiving a subassembly comprising a tension meter according to a first embodiment of the invention.

This intervention assembly 10 is intended to perform operations in a fluid exploitation well 12 in the subsoil 14.

The recovered fluid in the well 12 is for example a hydrocarbon such as oil or natural gas or another effluent, such as vapor, gas or water. Alternatively, the well 12 is an injection well in which a liquid or gas is injected.

The intervention assembly 10 is intended to perform operations and/or measurements at any point whatsoever of the well 12 from the surface 16.

The well 12 is formed in a cavity 18 positioned between the surface 16 and the fluid reservoir (not shown) situated at a given depth in a subterranean formation 14.

The well 12 generally includes a tubular outer pipe 20, designated using the term "casing," and for example formed by assembling tubes applied against the formations of the subterranean formation 14. Advantageously, the well 12 includes at least one inner tubular pipe 22 having a smaller diameter mounted in the outer tubular pipe 20. The inner tubular pipe is sometimes referred to as "production tubing".

The well 12 advantageously includes a wellhead 26 on the surface 16 that selectively closes the outer tubular pipe 20 and the inner tubular pipe 22. The wellhead 26 includes a plurality of selective access valves inside the outer tubular conduit 20 and inside the inner tubular conduit 22.

The intervention assembly 10 includes an intervention device for example for intervention and/or measurements in the well 12. The intervention device comprises a subassembly 30 intended to be lowered into the well 12 through the inner tubular pipe 22 and a line 32 for deploying the subassembly 30 in the well 12.

The intervention assembly 10 also includes a sealing and alignment assembly 34 of the line 32, mounted on the wellhead 26, a deployment assembly 36 of the line 32, arranged near the wellhead 26, and a control unit 38.

The intervention assembly 10 also includes communication means between the subassembly 30 and the surface 16, for example with the control unit 38. Said communication means are advantageously located within the line 32.

The line 32 is a solid cylindrical line having a smooth outer surface.

The line 32 extends between an upper end 41A, fastened on the surface deployment assembly 36, and a lower end 41B, intended to be introduced into the well 12. The subassembly 30 is suspended at the lower end 41B of the line 32.

The line 32 is generally referred to as "slick line".

The slick line advantageously has an electrically insulating coating on its outer surface, as disclosed in U.S. Pat. No. 7,652,592 of the applicant.

In a variation, a standard slick line is used with communication means other than those used in U.S. Pat. No. 7,652,592, such as acoustic or vibrational communication means.

In another variation, the line 32 is a mechanically reinforced electrical cable, generally referred to coil or coiled tubing (CT).

The length of the line 32 between the ends 41A, 41B may be greater than 1000 m and may be in particular between 1000 m and 10,000 m.

The well 12 contains a fluid 50. The fluid 50 has a hydrostatic pressure in the vicinity of the lower end 41B that amounts to a few hundreds of bars, typically between 10 and 2000 bars, where 1 bar equals 100,000 Pa.

The subassembly 30 includes a first element 84, for example a downhole tool intended to perform operations and/or measurements at the bottom of the well 12, a second element 80, for example a connecting line head connected with the line 32, and a tension meter 82 according to the invention extending between the first element 84 and the second element 80 along a longitudinal direction L of the well 12.

Depending on the local configuration of the well 12, the longitudinal direction L is inclined with respect to a vertical direction as shown in FIG. 1. In other sections of the well, the longitudinal direction L may be approximately vertical or horizontal, or may be inclined with a different angle than the angle shown on FIG. 1.

The downhole tool 84 is for example a mechanical actuator able to perform operations at the bottom of a well, such as the opening and closing of the valves, placement of elements, in particular the placement of a packer or another member. Depending on the local configuration of the well 12, the tool 84 advantageously includes sensors for detecting physical parameters such as the temperature, pressure, flow rate, depth, status of a depth valve, natural radiation of the ground (gamma radiation), location of casing collars (casing collar locator), or other measurement sensors. It can also include exploration devices such as a video camera.

The tool 84 can also include a means for inspecting the tubular pipe 20 or the tubular pipe 22, a tool for cleaning the tubular pipe 22, a tool for cutting the tubular pipe 22, a cutting tool or perforation means, or a centralizer.

The line connecting head 80 comprises an upper portion for attaching and connecting the line 32.

The tension meter 82 is mechanically connected on one side with the first element 84 and on the other side with the second element 80 along the longitudinal direction L in order to measure a mechanical tension F1 existing between the first element 84 and the second element 80.

"Mechanical tension" is to be understood as encompassing "traction or compression". Traction may be defined as a positive mechanical tension, whereas compression may be defined as a negative mechanical tension. The mechanical tension F1 to be measured may change from traction to compression depending on how the subassembly 30 is actually used or when the mechanical tension F1 is recorded.

The mechanical tension F1 may be expressed for example in Newtons, in kg, in pounds, or in their multiples such as DaN and tons.

Figure 2:
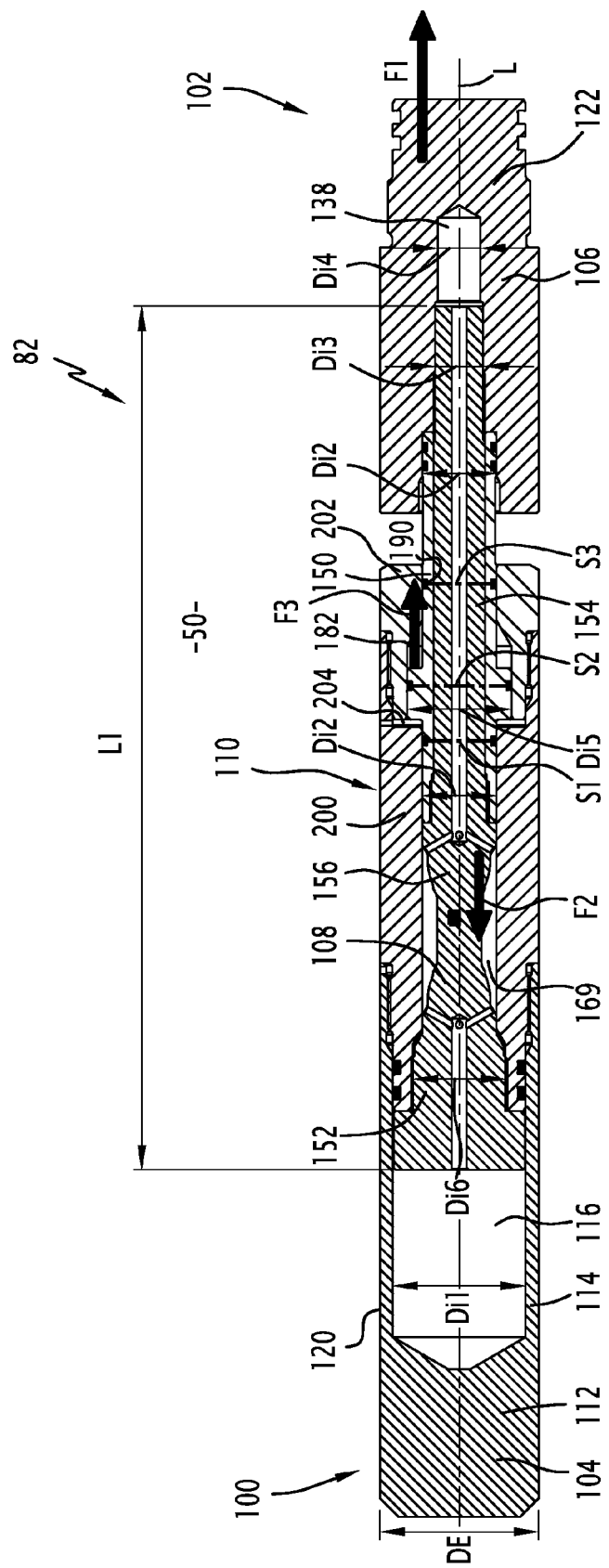
FIG. 2 is a longitudinal cross-sectional view of the tension meter shown in FIG. 1.
Figure 3:
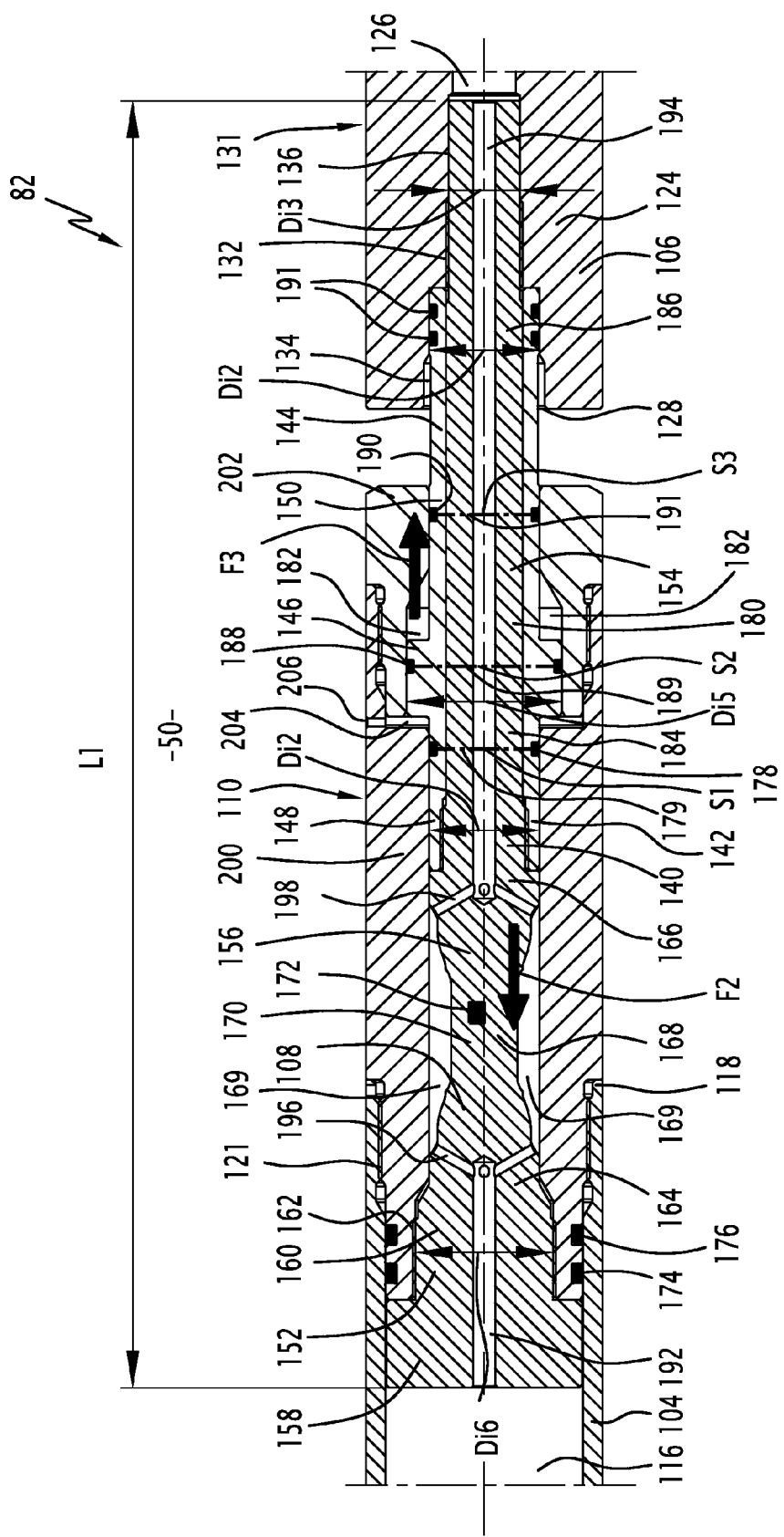
FIG. 3 is a detailed view of a central zone of the tension meter shown in FIGS. 1 and 2.

FIGS. 2 and 3 illustrate the tension meter 82 in more details. The longitudinal direction L is represented in a horizontal orientation to facilitate the reading of FIGS. 2 and 3. As described here above, this does not imply that the longitudinal direction L is actually horizontal when the tension meter 82 is being used.

The tension meter 82 extends between a distal end 100, on the left side of FIG. 2, and a proximal end 102, on the right side of FIG. 2, with respect to the line 32 (shown in FIG. 1).

The tension meter 82 has an approximately cylindrical general shape, advantageously with a circular basis having a diameter DE.

The tension meter 82 (FIG. 2) comprises a first part 104 defining the distal end 100, a second part 106, defining the proximal end 102, a bar 108 extending longitudinally between the first part 104 and the second part 106, and a hollow member 110 receiving the bar 108 along the longitudinal direction L.

The first part 104 is mechanically connected with the first element 84 shown on FIG. 1. The first part 104 comprises a distal portion 112 along the longitudinal direction L forming the distal end 100, and a proximal portion 114 forming a first cavity 116 having an opening 118 towards the proximal end 102.

The first part 104 has an outer surface 120 that is advantageously approximately cylindrical with a circular basis having the diameter DE.

The proximal portion 114 has a first inside thread 121 for connection with the hollow member 110.

The first cavity 116 is for example approximately cylindrical along the longitudinal direction L, with a circular basis having a diameter DI1. The first cavity 116 partially receives the hollow member 110 and the bar 108. A distal part of the first cavity 116 defines a first volume able to host electronic components or electrical lines (not shown). For example said first volume approximately extends over 20% to 80% of the first cavity volume 116 along the longitudinal direction L, preferably over 40% to 60% of the first cavity volume 116.

The second part 106 is mechanically connected with the second element 80 shown in FIG. 1. The second part 106 comprises a proximal portion 122 along the longitudinal direction L forming the proximal end 102, and a distal portion 124 forming a second cavity 126 having an opening 128 towards the distal end 100.

The second part 106 has an outer surface 130 that is advantageously approximately cylindrical, for example with a circular basis having the diameter DE.

The distal portion 124 has a second inside thread 132 for connection with the bar 108.

The second cavity 126 advantageously comprises a distal section 134, a middle section 136 and a proximal section 138 along the longitudinal direction L.

The distal section 134, the middle section 136 and the proximal section 138 are advantageously approximately cylindrical along the longitudinal direction L The distal section 134 for example has a circular basis with a diameter DI2. The middle section 136 for example has a circular basis with a diameter DI3 smaller than the diameter DI2. The proximal section 138 for example has a circular basis with a diameter DI4 smaller than the diameter DI3.

The distal section 134 and the middle section 136 partially receive the bar 108.

The proximal section 138 advantageously defines a second volume able to host electronic components or electrical lines (not shown).

In this example, the bar 108 (FIGS. 2 and 3) advantageously comprises a first inner piece 140 and a second outer piece 142, both extending along the longitudinal direction L, the second piece 142 having a through hole receiving the first piece 140, as shown in FIG. 3

The first piece 140 has a length L1 along the longitudinal direction L.

The second piece 142 covers the first piece 140 over a fraction of the length L1.

The second piece 142 comprises a hollow cylinder 144 extending along the longitudinal direction L and a radial protrusion 146 extending around the hollow cylinder 144.

The hollow cylinder 144 comprises a distal part 148 on one side of the radial protrusion 146 along the longitudinal direction L, and a proximal part 150 on the other side of the radial protrusion 146.

The hollow cylinder 144 has an outside diameter approximately equal to the diameter DI2 and an inside diameter approximately equal to the diameter DI3.

The radial protrusion 146 has an outside diameter DI5 larger than the diameter DI2.

The first piece 140 and the second piece 142 are in contact along the through hole. The second piece is for example screwed on the first piece 140.

As an alternative the bar 108 could consist of one single piece, or of more than two pieces.

Considered as a whole, the bar 108 comprises a first portion 152 mechanically connected with the first part 104, a second portion 154 mechanically connected with the second part 106, and an measurement portion 156 extending longitudinally between the first portion 152 and the second portion 154.

The bar 108 is free to elongate longitudinally within the hollow member 110 from the first portion 152 towards the proximal end 102, or to compress within the hollow member 110.

The first portion 152 comprises a first section 158 forming a distal head, and a second section 160 extending between the distal head 158 and the measurement portion 156.

The first section 158 for example has an approximately cylindrical shape, advantageously with a circular basis approximately having the DI1 diameter. The first section 158 is outside the hollow member 110

The second section 160 is received inside the hollow member 110. The second section 160 for example has an approximately cylindrical shape, for example with a circular basis having a diameter DI6. Advantageously, the diameter DI6 is smaller than the diameter DI1. The second section 160 also comprises a third outside thread 162 for connection with the hollow member 110.

The measurement portion 156 is advantageously symmetrical around the longitudinal direction L. The measurement portion 156 comprises a distal end 164, a proximal section 166, and a middle section 168 extending longitudinally between the distal end 164 and the proximal section 166.

The measurement portion 156, together with the hollow member 110, defines a first chamber 169.

The distal end 164 is for example approximately conical.

The middle section 168 has a cross section (that is to say a radial extension) that varies longitudinally. For example the middle section 168 becomes larger towards the distal end 164 and larger towards the proximal section 166, advantageously with a smooth narrowing towards a central zone 170.

The middle section 168 comprises at least one strain gauge 172 for measuring a longitudinal expansion of the measurement portion 156. Advantageously, the strain gauge 172 is located in the central zone 170.

The strain gauge 172 is fixed on the measurement portion 156.

The proximal section 166 is in contact with the hollow member 110. The proximal section 166 for example has a constant diameter along the longitudinal direction L and approximately equal to the diameter DI2.

The first chamber 169 extends around the measurement portion 156 along the longitudinal direction L.

The first chamber 169 is sealed by first sealing elements 174, 176, 178, 191 able to keep the first chamber 169 at a first chamber pressure, for example approximately at the atmospheric pressure.

By "atmospheric pressure", it is meant the average atmospheric pressure at sea level.

The first sealing elements 174, 176, 178, 191 comprise a first gasket 174, a second gasket 176 and a third gasket 178.

The first gasket 174 and the second gasket 176 are for example both located in an annular recess of the hollow member 110 and are in contact with the proximal portion 114 of the first part 104.

The third gasket 178 is for example located in an annular recess of the distal part 148 of the hollow cylinder 144 and is in contact with the hollow member 110. The third gasket 178 is at a junction between the measurement portion 156 and the second portion 154.

The third gasket 178 defines a first opening of the first chamber 169 towards the proximal end 102. The first opening 179 has a first surface S1. In the example shown in FIGS. 2 and 3, S1 is approximately a disk having the diameter DI2.

The second portion 154 of the bar 108 longitudinally comprises a chamber section 180 defining a second chamber 182 together with the hollow member 110, and, located on opposite sides of the chamber section 180, an intermediate section 184 extending between the chamber section 180 and the measurement portion 156, and an outside section 186.

The second chamber 182 is sealed by second sealing elements 188, 190 able to keep the second chamber 182 at a second chamber pressure, for example approximately equal to the first chamber pressure.

The second sealing elements comprise a fourth gasket 188 and a fifth gasket 190.

The fourth gasket 188 is located at a junction between the intermediate section 184 and the chamber section 180. The fourth gasket 188 extends within an annular recess of the radial protrusion 146 and is in contact with the hollow member 110.

The fourth gasket 188 defines a second opening 189 of the second chamber 182 towards the distal end 100. The second opening 189 has a second surface S2. In the example shown in FIGS. 2 and 3, S2 is approximately a disk with the DI5 diameter.

The fifth gasket 190 is located at a junction between the chamber section 180 and the outside section 186. The fifth gasket 190 extends within an annular recess of the radial protrusion 146 and is in contact with the hollow member 110.

The fifth gasket 190 defines a third opening 191 of the second chamber 182 towards the proximal end 102. The third opening 191 has a third surface S3. In the example shown in FIGS. 2 and 3, S3 is approximately a disk with the DI2 diameter.

Advantageously, the difference between S2 and S3 is approximately equal to S1 at +/−10%, preferably at +/−5%, more preferably at +/−2%, for example at +/−1%, in particular at +/−0.1%, more particularly at +/−0.01%.

In this example, the outside section 186 of the bar 108 is rigidly connected with the second part 106. The outside section 186 is for example screwed in the second part 106. The outside section 186 is hence able to move jointly with the second part 106 with regards to the first part 104 under the effect of the mechanical tension F1 applied between the first part 104 and the second part 106.

The elongation of the second part 106 with regards to the first part 104 is however small, i.e. lower than 0.2 mm.

As a result friction of the third gasket 178, the fourth gasket 188 and the fifth gasket 190 is minimized.

Advantageously the bar 108 comprises a first lumen 192 extending from the first cavity 106 to the measurement portion 156, a second lumen 194 extending from the second cavity 126 to the measurement portion 156, at least one channel 196 connecting the first lumen 192 with the first chamber 169, and at least another channel 198 connecting the second lumen 194 with first chamber 169. The first lumen 192, the second lumen 194, the channel 196 and the channel 198 advantageously provide a path for example for electrical cables (not shown) between the first cavity 116 and the second cavity 126, via the first chamber 169.

The first sealing elements 174, 176, 178, 191 also comprise at least one gasket 191 extending in an annular recess of the outside section 186 and in contact with the second part 106, in order to prevent the fluid 50 from entering the proximal section 138 of the second cavity 126.

In this example, the hollow member 110 comprises a main piece 200 extending longitudinally around the bar 108, and a proximal piece 202 forming an orifice crossed by the second portion 154.

The proximal piece 202 is for example screwed in the main piece 200.

The main piece 200, the proximal piece 202 and the intermediate section 184 define an intermediate fluid chamber 204, advantageously with an annular shape.

In the example shown in the Figures, the main piece 200, the inside thread 121 and the outside thread 162 mechanically connect the first part 104 with the first portion 152 of the bar 108.

The first chamber 169 and the second chamber 182 are located longitudinally on opposite sides of the intermediate fluid chamber 204.

As a variant, the hollow member 110 could be in one piece, or in more than two pieces.

The hollow member 110 is for example screwed in the first part 104.

The hollow member 110 for example has an outside shape that is approximately cylindrical with a circular basis advantageously having a diameter approximately equal to the diameter DE.

The hollow member 110 is in contact with clearance with the proximal part 150, with the distal part 148 and with the radial protrusion 146.

On the right side of FIG. 3, the hollow member 110 has an outside collar applied on the outer surface of the bar 108. The bar 108 longitudinally protrudes through said outside collar towards the proximal end 102. Advantageously said collar is in contact with the outer surfaces of both the chamber section 180 and the outside section 186 of the bar 108.

The hollow member 110 comprises a hole 206 opening into the intermediate fluid chamber 204 and allowing the intermediate section 184 to be in hydrostatic contact with the fluid 50.

Operation of the intervention assembly 10 shown in FIG. 1 will now be described, in particular the use of the tension meter 82 of the subassembly 30.

At first, the tension meter 82 is assembled. Thanks to the first sealing elements 174, 176, 178, 191, the first chamber 169 is kept at a pressure approximately equal to the atmospheric pressure. Thanks to the second sealing elements 188, 190, the second chamber 182 is also kept at a pressure approximately equal to the atmospheric pressure.

The tension meter 82 is then mounted in the subassembly 30. The first part 104 is attached to the first element 84 and the second part 106 is attached to the second element 80.

During operation of the intervention assembly 10, the subassembly 30 is lowered in the cavity 18 using the line 32, until a certain depth is reached, where the subassembly 30 is surrounded by the fluid 50 at the fluid pressure.

The tension meter 82, being mechanically connected with the first element 84, for example a downhole tool, and to the second element 80, for example a line head, is subject to the mechanical tension F1 existing between the first element 84 and the second element 80.

As the first portion 152 is mechanically connected with the first part 104 and the second portion 154 is mechanically connected with the second part 106, the measurement portion 156 of bar 108 is also subject to the mechanical tension F1. The bar 108 being free to expand or shrink within the hollow member 110, the measurement portion 156, in particular the middle section 168 equipped with the strain gauge 172, is subject to the mechanical tension F1.

Since the intermediate section 184 of the bar 108 is in hydrostatic contact with the fluid 50, the intermediate section 184 is subject to the fluid pressure.

In projection on the longitudinal direction L, the measurement portion 156 is the subject to a compression force F2 due to the pressure difference between the fluid pressure and the first chamber pressure applied to the first opening 179:

$$F2 = S1*(\text{fluid pressure} - \text{atmospheric pressure})$$

In projection on the longitudinal direction L, the intermediate section 184 and the chamber section 180 altogether are subject to a traction force F3 due to the pressure difference between the fluid pressure applied on the intermediate section 184 and the second chamber pressure applied on the chamber section 180:

$$F3 = -(S2-S3)*(\text{fluid pressure} - \text{atmospheric pressure})$$

F3 is negative, being a traction force.

The difference S2−S3 defines a hydrostatic surface SS2 of the second chamber 182:

$$SS2 = S2 - S3$$

The measurement portion 156 expands or shrinks due to F1+F2+F3

As the hydrostatic surface SS2 is approximately equal to the first surface S1, the contribution of the traction force F3 approximately offsets the contribution of compression force F2.

Advantageously, the compression force F2 and the traction force F3 compensate. By "compensate" it is meant that the compression force F2 and the traction force F3 are approximately equal in intensity in projection on the longitudinal direction L. The more the compression force F2 and the traction force F3 are equal, the more the tension meter is accurate. Advantageously, the compression force F2 and the traction force F3 are equal in intensity at +/−10%, preferably at +/−5%, more preferably at +/−2%, for example at +/−1%, in particular at +/−0.1%, more particularly at +/−0.01%.

The measurement portion 156 elongates or compresses due to mechanical tension F1 only, whereas the measurement portion 156 would be subject to F1+F2 in absence of the second chamber 182, or in case the second chamber 182 was at a pressure equal to the fluid pressure.

The strain gauge 172 transforms the change in length of the measurement portion 156 into an electrical signal representative of the mechanical tension F1. This can be advantageously performed on a continuous basis.

Information representative of this signal is carried to the control unit 38 via the communication means.

Thanks to the above described features, in particular the second chamber 182, the tension meter 82 provides measurements of the mechanical tension F1 which are not altered by a change in the fluid pressure, nor overwhelmed by the compression force F2 due to the fluid pressure. It is hence not necessary to measure the fluid pressure or to take it into account in order to determine the mechanical tension F1. As a result the tension meter 82 is very accurate. Also thanks to the first chamber 169 being sealed, the tension meter 82 requires no or less cleaning. The tension meter 82 is then easier to use, while remaining very economical.

The first lumen 192, the second lumen 194, the channel 196 and the channel 198 provide a convenient path for electrical cables going (FIG. 1) from the first element 84 or from the strain gauge 172 towards the second part 106 or the second element 80.

As a variant (not shown) there could be several chambers similar to the chamber 182 creating several forces in order to offset the compression force F2.

According to other variants (not shown), one or several of the following features could be implemented:
- the first element 84 and the first part 104 are interconnected to form a single element,
- the second element 80 and the second part 106 are interconnected to form a single element,
- the first part 104 and the first portion 152 are interconnected to form a single element,
- the second part 106 and the second portion 154 are interconnected to form a single element,
- the first part 104 and the hollow member 110 are interconnected to form a single element,
- the first portion 152 and the hollow member 110 are interconnected to form a single element.

Figure 4:
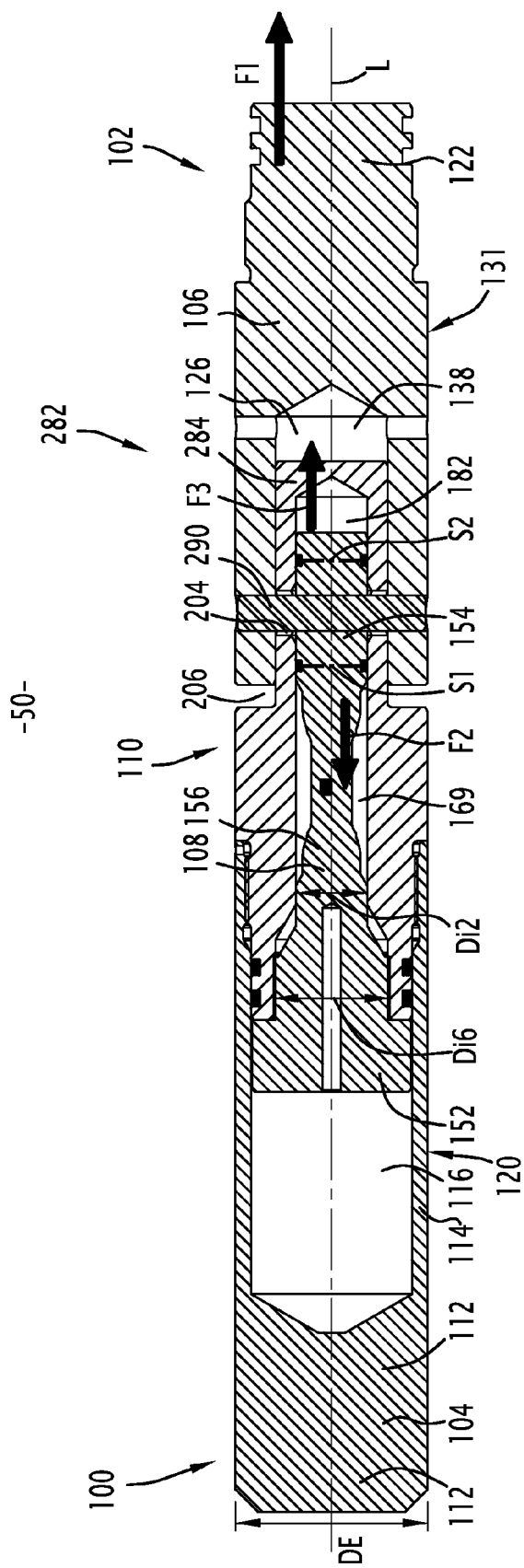
FIG. 4 is a longitudinal cross-sectional view of a tension meter according to a second embodiment of the invention.
Figure 5:
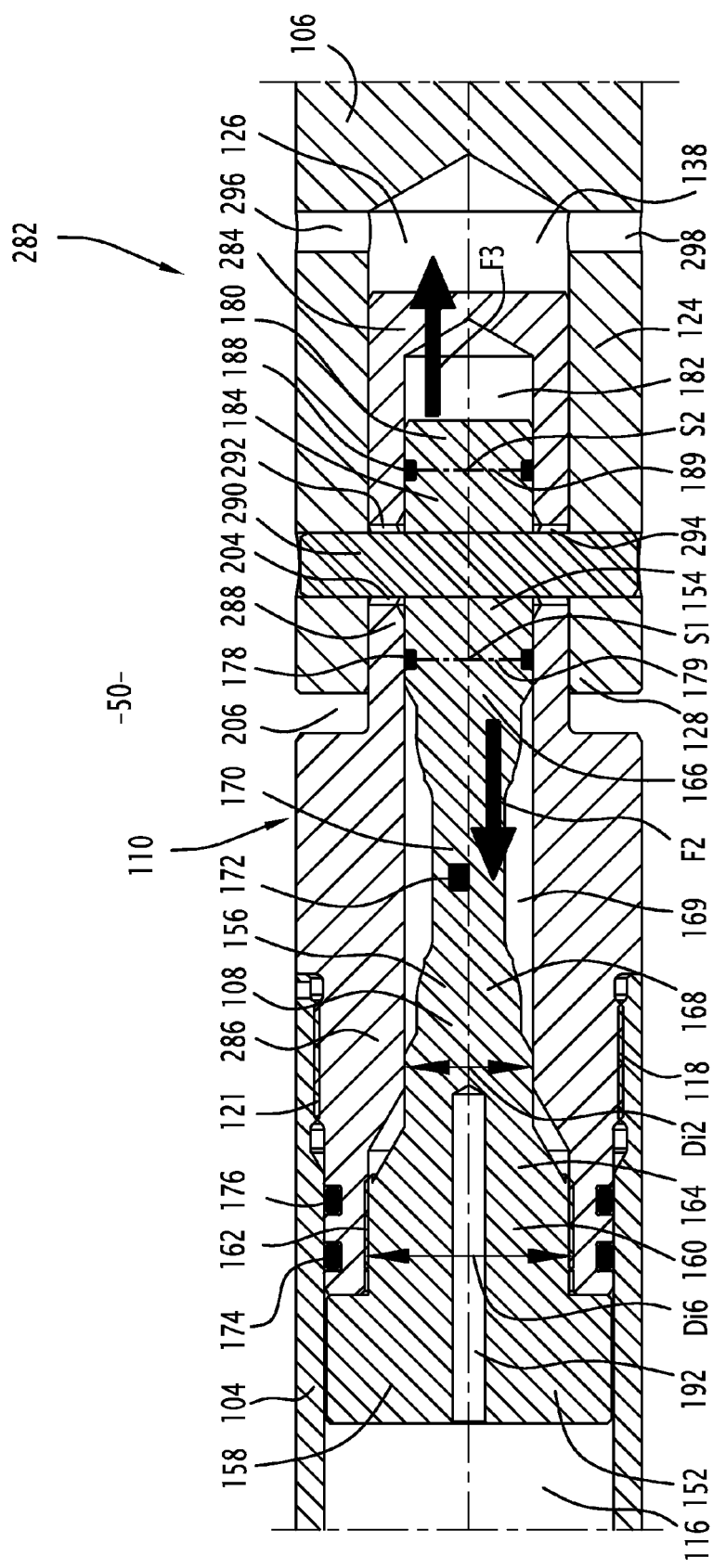
FIG. 5 is a detailed view of a central zone of the tension meter shown in FIG. 4.

A tension meter 282 corresponding to a second embodiment will now be described with reference to FIGS. 4 and 5.

Unless otherwise specified, the tension meter 282 is similar to the tension meter 82 represented in FIGS. 2 and 3 and similar parts have the same reference numbers.

The tension meter 282 mainly differs in that the hollow member 110 completely encloses the second portion 154. The hollow member 110 comprises a closing portion 284 which covers the chamber section 180 of the bar 108.

The hollow member 110 comprises a main portion 286 which is unchanged and an intermediate portion 288 extending between the closing portion 284 and the main part 286 along the longitudinal direction L.

As a result the second portion 154 of the bar 108 does not include an outside portion any more. The second portion 154 stops after the chamber section 180 towards the proximal end 102.

Also, the second portion 154 does not have a radial protrusion. The second portion 154 has an outer shape that is for example approximately cylindrical, advantageously with a circular basis having the DI2 diameter.

The second chamber 182 extends longitudinally between the chamber section 180 and the closing portion 284. The second chamber 182 does not have a third opening any more. The second opening 189, having the second surface S2, defines the hydrostatic surface SS2 of the second chamber 182, which is equal to the second surface S2.

Advantageously the second surface S2 is approximately equal to the first surface S1.

The second cavity 126 of the second part 106 receives the closing portion 284 and most of the intermediate part 288.

The intermediate section 184 is also received in the second cavity 126.

The second part 106 comprises a key 290 for connection with the second portion 154.

The key 290 is for example approximately perpendicular to the longitudinal direction L. The key 290 crosses the intermediate portion 288 of the hollow member 110 and the intermediate section 184 of the bar 108.

The key 290 rigidly connects the second part 106 with the intermediate section 184 of the second portion 154 of the bar 108. The intermediate section 184 is hence able to move jointly with the second part 106 with regards to the first part 104 under the effect of the mechanical tension F1 applied between the first part 104 and the second part 106.

The elongation of the second part 106 with regards to the first part 104 is however small, i.e. lower than 0.2 mm.

As a result friction of the third gasket 178 and the fourth gasket 188 is minimized.

The intermediate portion 288 has two opposite openings 292, 294 receiving the key 290 with sufficient clearance, so that the bar 108 remains free to elongates or compresses within the hollow member 110 under the mechanical tension F1.

The two openings 292, 294 are also able to allow the hydrostatic contact between the intermediate section 184 and the fluid 50.

The second part 106 also comprises two additional radial through holes 296, 298 opening into the proximal section 138 of the second cavity 126.

The operation of the tension meter 282 is similar to the operation of the tension meter 82 of FIGS. 2 and 3.

The shape of the second chamber 182 differs, but the second chamber 182 still create the traction force F3, with $F3=-S2*$(fluid pressure−atmospheric pressure)

As a result of the second surface S2 being approximately equal to the first surface S1, the traction force F3 still approximately offsets the compression force F2.

The invention claimed is:

1. A tension meter for measuring a mechanical tension (F1) along a longitudinal direction (L) between a first element and a second element deployed in a well containing a fluid having a fluid pressure, the tension meter comprising:
- a first part intended to be attached to the first element,
- a second part intended to be attached to the second element,
- a bar extending longitudinally between the first part and the second part, the bar comprising a first portion mechanically connected with the first part, a second portion mechanically connected with the second part, and a measurement portion extending longitudinally between the first portion and the second portion, and
- a hollow member receiving at least the measurement portion, the hollow member and the measurement portion defining a first chamber surrounding the measurement portion, the second portion being outside the first chamber and the bar being free to expand within the hollow member under the mechanical tension (F1) to be measured, wherein:
- the measurement portion includes at least one strain gauge,
- the tension meter includes first sealing elements for keeping the first chamber at a first chamber pressure, the measurement portion being subject to a compression force (F2) due to a difference between the fluid pressure and the first chamber pressure, and the tension meter includes means for converting the fluid pressure into a traction force (F3) applied on the second portion, wherein the compression force (F2) and the traction force (F3) compensate.

2. The tension meter according to claim 1, wherein:
the second portion of the bar comprises a chamber section, and an intermediate section extending between the chamber section and the measurement portion along the longitudinal direction (L) and intended to be in hydrostatic contact with the fluid, and
the hollow member and the chamber section define at least one second chamber, the tension meter having second sealing elements for keeping the second chamber at a second chamber pressure, approximately equal to the first chamber pressure.

3. The tension meter according to claim 2, wherein the hollow member includes at least one opening for allowing the hydrostatic contact of the intermediate section with the fluid.

4. The tension meter according to claim 2, wherein the hollow member and the intermediate section of the define an intermediate fluid chamber having at least an opening for enabling the fluid to enter the intermediate fluid chamber, the intermediate fluid chamber extending between the first chamber and the second chamber along the longitudinal direction (L), the first sealing elements separating the intermediate fluid chamber from the first chamber, the second sealing elements separating the intermediate fluid chamber from the second chamber.

5. The tension meter according to claim 1, wherein the means comprises:
at least one second chamber defined by the hollow member and a chamber section of the second portion of the bar, the tension meter having second sealing elements for keeping the second chamber at a second chamber pressure, approximately equal to the first chamber pressure,
at least one opening for allowing a hydrostatic contact of an intermediate section the second portion of the bar with the fluid, the intermediate section extending between the chamber section and the measurement portion along the longitudinal direction (L), and
an intermediate fluid chamber defined by the hollow member and the intermediate section of the bar, said opening enabling the fluid to enter the intermediate fluid chamber, the intermediate fluid chamber extending between the first chamber and the second chamber along the longitudinal direction (L), the first sealing elements separating the intermediate fluid chamber from the first chamber, the second sealing elements separating the intermediate fluid chamber from the second chamber.

6. The tension meter according to claim 2, wherein the second portion include an outside section protruding outside of the hollow member, the second portion being mechanically connected with the second part by the outside section.

7. The tension meter according to claim 6, wherein:
the first sealing elements include a first gasket, located between the measurement portion and the intermediate section, the first sealing elements defining a first opening of the first chamber, the first opening having a first surface (S1) in projection in a plane transverse to the longitudinal direction (L),
the second sealing elements include a second gasket, located between the intermediate section and the chamber section, the second sealing elements defining a second opening of the second chamber, the second opening having a second surface (S2) in projection in a plane transverse to the longitudinal direction (L), and
the second sealing elements include a third gasket, located between the chamber section and the outside section, the second sealing elements defining a third opening in the second chamber, the third opening having a third surface (S3) in projection in a plane transverse to the longitudinal direction (L), the second surface (S2) being larger than the third surface (S3).

8. The tension meter according to claim 7, wherein the difference between the second surface (S2) and the third surface (S3) defines a hydrostatic surface (SS2) of the second chamber which is approximately equal to the first surface (S1).

9. The tension meter according to claim 2, wherein the second part is mechanically connected with the intermediate section of the bar, the hollow member being closed longitudinally towards the second part by a closing portion extending radially, the second chamber extending between the closing portion and the chamber portion of the bar along the longitudinal direction (L).

10. The tension meter according to claim 9, wherein:
the first sealing elements include a first gasket, located between the measurement portion and the intermediate section, the first sealing elements defining a first opening of the first chamber, the first opening having a first surface (S1) in projection in a plane transverse to the longitudinal direction (L), and
the second sealing elements include a second gasket located between the intermediate section and the chamber section, the second sealing elements defining a second opening in the second chamber, the second opening having a second surface (S2) in projection in a plane transverse to the longitudinal direction (L).

11. The tension meter according to claim 10, wherein the second surface (S2) is approximately equal to the first surface (S1).

12. The tension meter according to claim 2, wherein the first chamber pressure is intended to be approximately equal to the atmospheric pressure.

13. A subassembly intended to be deployed in a well with a line along a longitudinal direction (L), the subassembly comprising at least a first element including a tool, and a second element including a connecting head, characterized in that the subassembly comprises a tension meter according to claim 1, the tension meter connecting the first element with the second element.

14. A method for measuring a mechanical tension (F1) along a longitudinal direction (L) between a first element and a second element, the method comprising the following steps:
providing a tension meter according to claim 1,
attaching the first part to the first element,
attaching the second part to the second element, and
deploying the first element and the second element in a well containing a fluid having a fluid pressure,
wherein it also comprises the steps of:
keeping the first chamber at a first chamber pressure,
subjecting the measurement portion to said compression force (F2) due to a difference between the fluid pressure and the first chamber pressure, and
converting the fluid pressure into said traction force (F3) applied on the second portion using said means of the tension meter, wherein the compression force (F2) and the traction force (F3) compensate.

* * * * *